US008618335B2

(12) United States Patent
Doi et al.

(10) Patent No.: US 8,618,335 B2
(45) Date of Patent: Dec. 31, 2013

(54) PROCESS FOR PREPARING AROMATIC ALDEHYDE COMPOUND

(75) Inventors: Takashi Doi, Ube (JP); Yoshihiro Yoshida, Ube (JP); Shinji Yasuda, Ube (JP); Yoshiyuki Watanabe, Ube (JP); Satoru Fujitsu, Ube (JP); Daisuke Douyama, Ube (JP)

(73) Assignee: Ube Industries Ltd., Ube-Shi (JP)

( * ) Notice: Subject to any disclaimer, the term of this patent is extended or adjusted under 35 U.S.C. 154(b) by 38 days.

(21) Appl. No.: 13/122,834

(22) PCT Filed: Oct. 6, 2009

(86) PCT No.: PCT/JP2009/067378
§ 371 (c)(1),
(2), (4) Date: Apr. 6, 2011

(87) PCT Pub. No.: WO2010/041643
PCT Pub. Date: Apr. 15, 2010

(65) Prior Publication Data
US 2012/0071672 A1    Mar. 22, 2012

(30) Foreign Application Priority Data

Oct. 7, 2008  (JP) ................. 2008-260550
Sep. 1, 2009  (JP) ................. 2009-201459

(51) Int. Cl.
*C07C 45/29*  (2006.01)
*C07D 317/54*  (2006.01)

(52) U.S. Cl.
USPC .......................................... 568/430; 549/436

(58) Field of Classification Search
USPC .......................................... 568/430; 549/436
See application file for complete search history.

(56) References Cited

FOREIGN PATENT DOCUMENTS

| EP | 0350395 A1 | 1/1990 |
|----|------------|--------|
| JP | 55-22615 A | 2/1980 |
| JP | 2-256641 A | 10/1990 |
| JP | 2006-517584 A | 7/2006 |
| WO | WO 2004/067484 A2 | 8/2004 |

OTHER PUBLICATIONS

G.D. Yadav et al., "Oxidation of benzyl alcohol under a synergism of phase transfer catalysis and heteropolyacids", Journal of Molecular Catalysis A: Chemical, 2001, vol. 172, pp. 135-149.

International Search Report for PCT/JP2009/067378, mailed on Dec. 22, 2009.
Jianwei Ma et al., "An effective tri-phasic catalytic system for oxidation of benzyl alcohol under phase transfer conditions", Catalysis Letters, 1992, vol. 15, pp. 275-279.
Kazuhiko Sato et al., "A Practical Method for Alcohol Oxidation with Aqueous Hydrogen Peroxide under Organic Solvent-and Halide-Free Conditions", Bulletin of the Chemical Society of Japan, 1999, vol. 72, pp. 2287-2306.
O. Bortolini et al., "Metal Catalysis in Oxidation by Peroxides. Molybdenum-and Tungsten-Catalyzed Oxidations of Alcohols by Diluted Hydrogen Peroxide under Phase-Transfer Conditions", Journal of Organic Chemistry, 1986, vol. 51, pp. 2661-2663.
Jacobson et al., "Oxidation of Alcohols by Molybdenum and Tungsten Peroxo Complexes," J. Org. Chem., vol. 44, No. 6, pp. 921-924, 1979.
Trost et al., "Chemoselectivity in Molybdenum Catalyzed Alcohol and Aldehyde Oxidations," Tetrahedron Letters, vol. 25, No. 2, pp. 173-176, 1984.
The Office Action, dated Nov. 12, 2013, issued in the corresponding Japanese Patent Application No. 2010-532914.

*Primary Examiner* — Sikarl Witherspoon
(74) *Attorney, Agent, or Firm* — Birch, Stewart, Kolasch & Birch, LLP

(57) ABSTRACT

An object of the present invention is to provide an industrially advantageous process for preparing a benzaldehyde compound from a benzyl alcohol compound with high yield.
The present invention relates to a process for preparing an aromatic aldehyde compound represented by the formula (2);

[Formula 10]

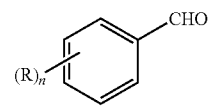

(2)

which comprises reacting an aromatic methyl alcohol compound represented by the formula (1);

[Formula 9]

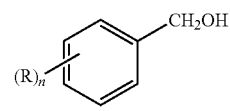

(1)

and a peroxide under a pH value of a reaction solution being pH 0.01 or higher and less than 10 in the presence of at least one metallic compound selected from a molybdenum compound and a tungsten compound, a quaternary ammonium salt and an organic phosphonium salt.

18 Claims, No Drawings

PROCESS FOR PREPARING AROMATIC ALDEHYDE COMPOUND

TECHNICAL FIELD

The present invention relates to a process for preparing an aromatic aldehyde compound which comprises the reaction of an aromatic methyl alcohol compound and a peroxide under a pH value of a reaction solution being pH 0.01 or higher and less than 10, in the presence of at least one metal compound selected from a molybdenum compound and a tungsten compound, and at least one salt selected from at least one salt selected from a quaternary ammonium salt and an organic phosphonium salt.

The aromatic aldehyde compound obtained by the preparation process of the present invention is a compound useful for various kinds of chemical products, for example, such as medical and agricultural chemicals and organic materials, and their starting intermediates.

BACKGROUND ART

Heretofore, as a method for preparing an aromatic aldehyde compound from an aromatic methyl alcohol compound, there have been well known, for example, a method of oxidizing a primary alcohol by using a metal oxide such as manganese oxide and pyridinium chlorochromate (PCC), etc. (for example, see Non-Patent Literature 1 and Non-Patent Literature 2.) or a reaction of Swern oxidation, etc. (for example, see Non-Patent Literature 3.). However, these reactions involve problems for carrying out the methods industrially because the reaction is carried out by using a metal reagent having high toxicity, or wastes occurs such as dimethylsulfide which accompanies bad smell after termination of the reaction so that environmental load is large.

On the other hand, a method of utilizing hydrogen peroxide has attracted attention in recent years because handling of hydrogen peroxide is easy, it can be decomposed to harmless water after the reaction, and further it is inexpensive (for example, see Patent Literature 1.).

[Patent Literature 1] JP H11-158107A
[Non-Patent Literature 1] Organic Letters, Vol. 5, 4725 (2003)
[Non-Patent Literature 2] J. Org. Chem., Vol. 69, 1453 (2004)
[Non-Patent Literature 3] Tetrahedron, Vol. 34, 1651 (1978)

DISCLOSURE OF THE INVENTION

Problems to be Solved by the Invention

For example, in Patent Literature 1, as a method for preparing a carbonyl compound such as an aldehyde, etc., by reacting a primary alcohol and hydrogen peroxide, a method of using a sodium tungstate/quaternary ammonium hydrogen sulfate catalyst has been reported. When the present inventors has actually synthesized piperonal which is an aromatic aldehyde compound by using this method, but the yield was 24.9%, so that this method is not satisfied in view of an industrial preparation method very well.

An object of the present invention is to provide a process for preparing an aromatic aldehyde compound from an aromatic methyl alcohol compound with good yield by an industrially advantageous process which can provide the product with high conversion and high reaction selectivity.

Means to Solve the Problems

The problem of the present invention can be solved by a process for preparing an aromatic aldehyde compound represented by the formula (2):

[Formula 2]

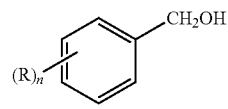

(2)

(wherein R represents a halogen atom, a hydrocarbon group having 1 to 12 carbon atoms, an alkyloxy group having 1 to 12 carbon atoms, a phenyloxy group, a naphthyl-oxy group, a benzyloxy group or a phenethyloxy group, each group of which may have a substituent(s); n is an integer of 0 to 5; and when n is 2 or more, Rs may form a ring by combining with each other.)

which comprises reacting an aromatic methyl alcohol compound represented by the formula (1):

[Formula 1]

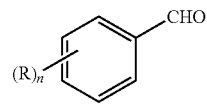

(1)

(wherein R and n have the same meanings as defined above.) and a peroxide under a pH value of a reaction solution being a pH of 0.01 or higher and less than 10, in the presence of at least one metallic compound selected from a molybdenum compound and a tungsten compound and at least one salt selected from a quaternary ammonium salt and an organic phosphonium salt.

Effects of the Invention

According to the preparation process of the present invention, from various aromatic methyl alcohol compounds, corresponding aromatic aldehyde compounds can be obtained with good yield as compared with the conventional methods.

Also, the preparation process of the present invention is a preparation process containing an operation method which is simple and easy, and which is less load to environment since an amount of harmful waste is little.

Further, the preparation process of the present invention gives an objective aromatic aldehyde compound with good yield, for example, when an aqueous hydrogen peroxide is used as a peroxide, and even when an amount of the aqueous hydrogen peroxide to be used is an equivalent molar amount to that of an aromatic methyl alcohol compound, so that this is a preparation process which can also relief against the operation risk accompanied by using an excessive amount of a peroxide in the conventional method.

BEST MODE TO CARRY OUT THE INVENTION

The aromatic aldehyde compound represented by the formula (2) of the present invention can be obtained by reacting an aromatic methyl alcohol compound and a peroxide under a pH value of a reaction solution being a pH of 0.01 or higher and less than 10 in the presence of at least one metallic compound selected from a molybdenum compound and a tungsten compound and at least one salt selected from a quaternary ammonium salt and an organic phosphonium salt.

In the reaction of the present invention, the aromatic methyl alcohol compound as the starting material is represented by the above-mentioned formula (1). In the formula, R represents a halogen atom, a hydrocarbon group having 1 to 12 carbon atoms, an alkyloxy group having 1 to 12 carbon atoms, a phenyloxy group, a naphthyl-oxy group, a benzyloxy group or a phenethyloxy group. Additionally, these groups may have a substituent(s). Also, n is an integer of 0 to 5. Further, when n is 2 or more, Rs may form a ring by combining with each other.

In the formula (1), in R, the halogen atom means a fluorine atom, chlorine atom, bromine atom or iodine atom.

In the formula (1), in R, the above-mentioned hydrocarbon group having 1 to 12 carbon atoms may be mentioned a linear, branched or cyclic aliphatic group (for example, a methyl group, ethyl group, propyl group, isopropyl group, cyclopropyl group, n-butyl group, isobutyl group, t-butyl group, cyclobutyl group, n-pentyl group, i-pentyl group, s-pentyl group, amyl group, cyclopentyl group, n-hexyl group and cyclohexyl group, etc.), an aromatic group (for example, a phenyl group and naphthyl group, etc.), and an aliphatic group to which an aromatic group is bonded (an aralkyl group: for example, a benzyl group, phenethyl group, etc.). These groups contain various kinds of isomers.

In the formula (1), in R, the above-mentioned alkyloxy group having 1 to 12 carbon atoms is a group in which a linear, branched or cyclic aliphatic group is bonded to an oxygen atom (for example, a methoxy group, ethoxy group, propyloxy group, isopropyloxy group, cyclopropyloxy group, n-butyloxy group, isobutyloxy group, t-butyloxy group, cyclobutyloxy group, n-pentyloxy group, i-pentyloxy group, s-pentyl-oxy group, amyloxy group, cyclopentyloxy group, n-hexyloxy group and cyclohexyloxy group, etc.). These groups contain various kinds of isomers.

Also, the above-mentioned hydrocarbon group, alkyloxy group, phenyloxy group, naphthyloxy group, benzyloxy group or phenethyloxy group may have a substituent(s). As the substituent(s), there may be mentioned a halogen atom, an alkyl group having 1 to 6 carbon atoms (including various kinds of isomers), and an alkyloxy group having 1 to 6 carbon atoms (including various kinds of isomers). One or more kinds of these substituents may be bonded to the above-mentioned hydrocarbon group.

Further, when n is 2 or more, Rs may be combined with each other to form a ring with the adjacent carbon atoms of the benzene ring. Such a ring may be mentioned, for example, a chromane ring, alkylenedioxy ring, naphthalene ring, indane ring, tetrahydronaphthalene ring, etc., which are combined with the benzene ring of the formula (1).

The aromatic aldehyde compound obtained by the preparation process of the present invention is represented by the above-mentioned formula (2). In the formula (2), R and n have the same meanings as in the above-mentioned formula (1).

The aromatic aldehyde compound represented by the formula (2) may be preferably mentioned benzaldehyde, naphthylaldehyde, tetrahydronaphthylaldehyde, chromanecarbaldehyde, and compounds shown by the following formulae (3) to (7).

[Formula 3]

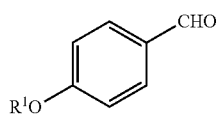

(3)

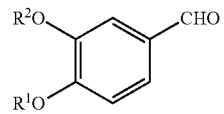

(4)

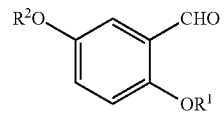

(5)

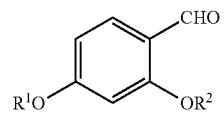

(6)

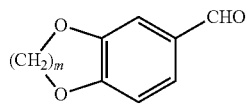

(7)

(wherein $R^1$ and $R^2$ each represent a hydrogen atom, a hydrocarbon group having 1 to 12 carbon atoms, an alkyl group having 1 to 12 carbon atoms, a phenyl group, a naphthyl group, a benzyl group or a phenethyl group, each group of which may have a substituent(s); and in is 1 or 2)

Here, in the formula (3) to formula (7), $R^1$ and $R^2$ each represent a hydrogen atom, a hydrocarbon group having 1 to 12 carbon atoms, an alkyl group having 1 to 12 carbon atoms, a phenyl group or a naphthyl group, a benzyl group or a phenethyl group. Additionally, these groups may have a substituent(s). m is 1 or 2.

The hydrocarbon group having 1 to 12 carbon atoms, the alkyl group having 1 to 12 carbon atoms, the phenyl group, the naphthyl group, the benzyl group or the phenethyl group, and the substituent(s) which may be bonded to the above groups in $R^1$ and $R^2$ have the same meanings as defined in the above-mentioned formula (1).

The aromatic aldehyde compound represented by the formula (2) may be preferably mentioned a compound wherein R is an aliphatic group having 1 to 4 carbon atoms or a benzyl group, the compounds of the formulae (3) to (6) and the compound of the formula (7) wherein m is 1 (piperonal).

The peroxide to be used in the reaction of the present invention, there may be mentioned, for example, an inorganic peroxide such as aqueous hydrogen peroxide, a persulfate compound (for example, persulfuric acid, sodium hydrogen persulfate, potassium hydrogen persulfate, etc.), etc., or an organic peroxide such as t-butyl hydro-peroxide, meta-chloroperbenzoic acid, performic acid, peracetic acid and perpropionic acid, etc., and hydrogen peroxide is preferably used. The above-mentioned peroxide may be used alone or may be used in admixture of two or more kinds. The peroxide may be used as such, or may be used by dissolving or suspending in water, or an organic solvent such as an alcohol, etc., or a mixed solvent thereof.

An amount of the peroxide to be used is preferably 0.1 to 5 mol, more preferably 0.2 to 3 mol, further preferably 0.8 to 2.1 mol, particularly preferably 0.9 to 1.5 mol, and particularly more preferably 0.95 to 1.3 mol based on 1 mol of the aromatic methyl alcohol compound.

It has been known that, for example, an aqueous hydrogen peroxide is used as a peroxide in an excessive amount, the excessive portion are decomposed during the reaction or after completion of the reaction to generate an oxygen. When the amount of the generating oxygen becomes larger and larger, it causes a serious problem in terms of safety operation because it forms a flammable or explosive mixed gas with a vapor comprising a solvent, an aromatic methyl alcohol compound and an aromatic aldehyde compound.

Thus, according to the process of the present invention, it is desired to use hydrogen peroxide as little as possible with the progress of the reaction within the range of not exceeding 5 mol based on 1 mol of the aromatic methyl alcohol compound.

On the other hand, in case of an amount of the hydrogen peroxide to be used is less than 0.8 mol based on 1 mol of the aromatic methyl alcohol compound, decomposition or side reaction of the aromatic methyl alcohol compound occurs when the remaining unreacted aromatic methyl alcohol compound is separated or recovered by distillation, etc., after completion of the reaction. In particular, in the case of using an aromatic methyl alcohol compound having an electron donative substituent such as an alkoxy group or methylenedioxy group at the aromatic ring, it sometimes becomes a serious problem. Accordingly, an amount of the hydrogen peroxide to be used is desirably 0.8 mol or more based on 1 mol of the aromatic methyl alcohol compound.

When an aqueous hydrogen peroxide is used as the above-mentioned peroxide, the concentration thereof is not particularly limited, and it is preferably 10 to 90% aqueous solution, more preferably 30 to 80% aqueous solution, and further preferably 50 to 70% aqueous solution.

Also, the process of the present invention may be carried out, for example, by adding an aqueous hydrogen peroxide solution to a reaction system finally which is different from an operation method disclosed in Patent Literature 1. That is, the present invention is a preparation process which may be carried out by adding a peroxide dropwise continuously or stepwisely, for the purpose of, for example, confirming the condition of consumed peroxide during the reaction or controlling the progress of the reaction.

Accordingly, in the process of the present invention, by carrying out the operation method as mentioned above, it may be used, for example, 30% aqueous hydrogen peroxide solution which is a commercially available product as such. Moreover, even when an aqueous solution with a higher concentration such as a 60% aqueous hydrogen peroxide solution, etc., is used, the aromatic aldehyde compound can be prepared by a process which is safer and an amount of waste after the reaction is reduced.

The reaction of the present invention is carried out in the presence of at least one metallic compound selected from a molybdenum compound and a tungsten compound.

The molybdenum compound to be used in the reaction of the present invention may be mentioned, for example, molybdenum hydroxide, an alkali molybdate compound (for example, lithium molybdate, potassium molybdate, sodium molybdate, etc.), an alkaline earth metal molybdate compound (for example, calcium molybdate, barium molybdate, etc.), a molybdenum compound comprising molybdenum and an element of Group IIIb, IVb, Vb or VIb (for example, cerium molybdate, iron molybdate, etc.), ammonium molybdate, molybdenum dioxide, molybdenum trioxide, molybdenum trisulfide, molybdenum hexachloride, molybdenum silicate, molybdenum boride, molybdenum nitride, molybdenum carbide, phosphomolybdic acid, an alkali phosphomolybdate compound (for example, sodium phosphomolybdate, etc.), ammonium phosphomolybdate, molybdenum hexacarbonyl, silver molybdate, cobalt molybdate, etc. These molybdenum compounds may be a hydrate, for example, sodium molybdate dihydrate, potassium molybdate dihydrate, etc.

The molybdenum compound is preferably a molybdenum compound which can easily generate a molybdate anion among the above-mentioned compounds, and concrete examples thereof may be more preferably mentioned an alkali molybdate compound, molybdenum dioxide, molybdenum trioxide, phosphomolybdic acid, an alkali phosphomolybdate compound and molybdenum hexacarbonyl, particularly preferably sodium molybdate dihydrate, potassium molybdate dihydrate, molybdenum dioxide, molybdenum trioxide and molybdenum hexacarbonyl, and particularly more preferably sodium molybdate dihydrate, potassium molybdate dihydrate, molybdenum dioxide and molybdenum hexacarbonyl.

The tungsten compound to be used in the reaction of the present invention may be mentioned, for example, tungstic acid, an alkali tungstate compound (for example, sodium tungstate, potassium tungstate, etc.), a tungsten compound comprising tungsten and an element of Group IIIb, IVb, Vb or VIb (for example, cobalt(II) tetraoxotungstate (IV), ferric oxytungstate, etc.), ammonium tungstate, tungsten dioxide, tungsten trioxide, tungsten trisulfide, tungsten hexachloride, tungsten silicate, tungsten boride, tungsten nitride, tungsten carbide, phosphotungstic acid, an alkali phosphotungstate compound (for example, sodium phosphotungstate, etc.), ammonium phosphotungstate, tungsten hexacarbonyl, silver tungstate, cobalt tungstate, etc. These tungsten compounds may be a hydrate, for example, sodium tungstate dihydrate, potassium tungstate dihydrate, etc.

The tungsten compound is preferably a tungsten compound which can easily generate a tungstate anion among the above-mentioned compounds, and concrete examples thereof may be more preferably mentioned an alkali tungstate compound, tungsten trioxide, phosphotungstic acid, an alkali phosphotungstate compound and tungsten hexacarbonyl, and particularly preferably sodium tungstate dihydrate and potassium tungstate dihydrate.

At least one metallic compound selected from the above-mentioned molybdenum compound and tungsten compound each may be used singly, or may be used in admixture of two or more kinds selected from the respective compounds. Also, to carry out the reaction of the present invention more effectively, it may be carried out, for example, by using a metal catalyst of a transition metal, etc., such as scandium, cerium, titanium, zirconium, iron, aluminum, ruthenium, nickel, palladium, platinum, copper, silver, gold, zinc, bismuth, antimony, etc., in combination. Moreover, the molybdenum compound and the tungsten compound may be used as such, or may be used by dissolving or suspending in water, an organic solvent such as an alcohol, etc., or a mixed solvent thereof.

An amount of at least one metallic compound to be used selected from the molybdenum compound and the tungsten compound of the present invention is preferably 0.0001 to 0.10 mol, more preferably 0.0005 to 0.08 mol, and particularly preferably 0.001 to 0.05 mol based on 1 mol of the aromatic methyl alcohol compound.

The reaction of the present invention is carried out in the presence of at least one salt selected from a quaternary ammonium salt and an organic phosphonium salt.

The quaternary ammonium salt to be used in the present invention may be mentioned a quaternary ammonium hydrogen sulfate and/or a quaternary ammonium halide.

The quaternary ammonium hydrogen sulfate may be mentioned, for example, tetrapropyl ammonium hydrogen sulfate, tetrabutyl ammonium hydrogen sulfate, tetra-n-hexyl ammonium hydrogen sulfate, benzyltrimethyl ammonium hydrogen sulfate, benzyltriethyl ammonium hydrogen sulfate, lauryltrimethyl ammonium hydrogen sulfate, stearyltrimethyl ammonium hydrogen sulfate, dilauryldimethyl ammonium hydrogen sulfate, methyltrioctyl ammonium hydrogen sulfate, ethyltrioctyl ammonium hydrogen sulfate, N-laurylpyridinium hydrogen sulfate, N-cetylpyridinium hydrogen sulfate, N-laurylpicolinium hydrogen sulfate, N-cetylpicolinium hydrogen sulfate, N-laurylquinolium hydrogen sulfate and N-cetylquinolium hydrogen sulfate, etc.

The quaternary ammonium halide is preferably a quaternary ammonium halide of chloride or bromide, and may be mentioned, for example, tetramethyl ammonium chloride, tetramethyl ammonium bromide, tetraethyl ammonium chloride, tetraethyl ammonium bromide, tetrapropyl ammonium chloride, tetrapropyl ammonium bromide, tetrabutyl ammonium chloride, tetrabutyl ammonium bromide, benzyltriethyl ammonium chloride, benzyltriethyl ammonium bromide, lauryltrimethyl ammonium chloride, stearyltrimethyl ammonium chloride, dilauryldimethyl ammonium chloride, methyltri-octyl ammonium chloride, ethyltrioctyl ammonium chloride, N-laurylpyridinium chloride, N-cetylpyridinium chloride, N-laurylpicolinium chloride, N-cetylpicolinium chloride, N-laurylquinolium chloride and N-cetylquinolium chloride, etc.

These quaternary ammonium salts may be a hydrate.

The quaternary ammonium salt may be more preferably mentioned tetrabutyl ammonium hydrogen sulfate, tetra-n-hexyl ammonium hydrogen sulfate, tetrabutyl ammonium chloride and tetrabutyl ammonium bromide.

The above-mentioned quaternary ammonium salts may be used singly, or in admixture of two or more kinds. Also, the quaternary ammonium salt may be used as such, or may be used by dissolving in water, an organic solvent such as an alcohol, etc., or a mixed solution thereof.

An amount of the quaternary ammonium salt to be used in the present invention is preferably 0.0001 to 0.10 mol, more preferably 0.0005 to 0.08 mol, and particularly preferably 0.001 to 0.05 mol based on 1 mol of the aromatic methyl alcohol compound.

The organic phosphonium salt to be used in the present invention may be mentioned an organic phosphonium salt having an aromatic substituent(s) and/or alkyl substituent(s).

The organic phosphonium salt may be mentioned, for example, tetrabutylphosphonium chloride, tetrabutylphosphonium bromide, tetraphenylphosphonium chloride, tetraphenylphosphonium bromide, tetraphenylphosphonium iodide, tetramethylphosphonium chloride, tetramethylphosphonium bromide, tetramethylphosphonium iodide, etc., and preferably tetrabutylphosphonium chloride, tetrabutylphosphonium bromide, tetraphenylphosphonium chloride and tetraphenylphosphonium bromide.

The above-mentioned organic phosphonium salt may be used alone or in admixture of two or more kinds. Also, the organic phosphonium salt may be used as such, or may be used by dissolving or suspending in water, an organic solvent such as an alcohol, etc., or a mixed solvent thereof.

An amount of the organic phosphonium salt to be used in the present invention is preferably 0.0001 to 0.10 mol, more preferably 0.0005 to 0.08 mol, and particularly preferably 0.001 to 0.05 mol based on 1 mol of the aromatic methyl alcohol compound.

The reaction of the present invention may be carried out by adding at least one buffer selected from a phosphoric acid compound, a boric acid compound and a carbonic acid compound to the reaction mixture for the purpose of, for example, making pH adjustment simple and easy, stabilizing a peroxide, etc.

The phosphoric acid compound to be used in the reaction of the present invention may be mentioned, for example, phosphoric acid (orthophosphoric acid, pyrophosphoric acid, metaphosphoric acid), an alkali metal salt of phosphoric acid (for example, sodium phosphate, potassium phosphate, etc.), an alkaline earth metal salt of phosphoric acid (for example, calcium phosphate, etc.), an alkali metal salt of hydrogen phosphate compound (for example, sodium monohydrogen phosphate, sodium dihydrogen phosphate, potassium monohydrogen phosphate, potassium dihydrogen phosphate, etc.), and ammonium phosphate.

The boric acid compound to be used in the reaction of the present invention may be mentioned, for example, boric acid (orthoboric acid, metaboric acid, tetraboric acid), an alkali metal salt of boric acid, an alkaline earth metal salt of boric acid (for example, potassium borate calcium tetraborate, etc.), and ammonium borate.

The carbonic acid compound to be used in the reaction of the present invention may be mentioned, for example, carbonic acid, an alkali metal salt of carbonic acid (for example, sodium carbonate, potassium carbonate, etc.), an alkaline earth metal salt of carbonic acid (for example, calcium carbonate, etc.), an alkali metal salt of a hydrogen carbonate compound (for example, sodium hydrogen carbonate, potassium hydrogen carbonate, etc.).

The above-mentioned phosphoric acid compound, boric acid compound and carbonic acid compound may be used alone or in admixture of two or more kinds. These compounds may be used as such, or may be used by dissolving or suspending in water, an organic solvent such as an alcohol, etc., or a mixed solvent thereof.

Among the above-mentioned compounds, a phosphoric acid compound is preferably used in the view point of stability of the peroxide during the reaction. An amount of at least one buffer selected from a phosphoric acid compound, a boric acid compound and a carbonic acid compound to be used is preferably 0.0001 to 0.005 mol, more preferably 0.0003 to 0.05 mol, and particularly preferably 0.0005 to 0.03 mol based on 1 mol of the aromatic methyl alcohol compound.

The reaction of the present invention can be carried out in the absence of a solvent or in the presence of a solvent.

The solvent to be used is not particularly limited so long as it does not inhibit the reaction, and there may be mentioned, for example, water, formic acid, aliphatic carboxylic acids (for example, acetic acid, propionic acid, trifluoroacetic acid, etc.), organic sulfonic acids (for example, methanesulfonic acid, trifluoromethanesulfonic acid, etc.), alcohols (for example, methanol, ethanol, isopropyl alcohol, t-butyl alcohol, ethylene glycol, triethylene glycol, etc.), ketones (for example, acetone, butanone, cyclohexanone), aliphatic hydrocarbons (for example, n-pentane, n-hexane, n-heptane, cyclohexane, etc.), amides (for example, N,N-dimethylformamide, N,N-dimethylacetamide, N-methylpyrrolidone, etc.), ureas (N,N'-dimethylimidazolidinone, etc.), ethers (for example, diethyl ether, diisopropyl ether, tetrahydrofuran, dioxane, 1,2-methylene-dioxybenzene, etc.), aromatic hydrocarbons (for example, benzene, toluene, xylene, etc.), halogenated aromatic hydrocarbons (for example, chlorobenzene, 1,2-dichloro-benzene, 1,3-dichlorobenzene, 1,4-dichlorobenzene, etc.), nitrated aromatic hydro-carbons (for example, nitrobenzene, etc.), halogenated hydrocarbons (for example, methylene chloride, chloroform, carbon tetrachloride, 1,2-dichloroethane, etc.), carboxylates (for example, ethyl acetate, propyl acetate, butyl acetate, etc.), nitriles (for example, acetonitrile, propionitrile, benzonitrile, etc.), sulfoxides (for example, dimethylsulfoxide, etc.), sulfones (for example, sulfolane, etc.) and the like. These solvents may be used alone or in admixture of two or more kinds.

When the above-mentioned solvent(s) is/are used, an amount to be used is optionally controlled depending on the uniformity of the reaction solution or stirrability thereof, and it is, for example, preferably 0.1 to 1000 g, more preferably 0.3 to 500 g, particularly preferably 0.5 to 200 g, and particularly more preferably 0.5 to 100 g based on 1 g of the aromatic methyl alcohol compound.

A range of the pH value of the reaction solution of the present invention is a pH of 0.01 or higher and less than 10. When a molybdenum compound is used as the metallic compound, it is preferably a pH of 0.01 to 10, more preferably a pH of 0.01 or higher and less than 9, particularly preferably a pH of 0.1 or higher and less than 9, particularly more preferably a pH of 0.5 or higher and less than 9, particularly more preferably a pH of 0.8 or higher and less than 9, and particularly preferably a pH of 1 or higher and less than 9. On the other hand, when a tungsten compound is used as the metallic compound, it is preferably a pH of 3 or higher and less than 8, more preferably a pH of 4 to 7.5, and particularly preferably a pH of 5 to 7.

The reaction of the present invention is considered to be carried out with good yield, for example, even when a pH value of the reaction solution is pH of less than 0.01. However, an object of the present invention is to provide an industrially preferable preparation process, and it is not actually usual to use a device which can accurately measure a pH of less than 0.01 for a commercial purpose. Accordingly, a pH of 0.01 or more which is detection limit of commercially available measurement device is determined as a lower limit of the pH value of the reaction solution to be used in the reaction of the present invention. On the other hand, in case of the pH value of the reaction solution is a pH of 10 or more, the peroxide which is a starting material is easily decomposed so that it is not preferred. Accordingly, in the present invention, by carrying out the reaction within the above-mentioned pH range of the reaction solution, an aromatic aldehyde compound can be prepared with higher conversion, higher reaction selectivity and good yield as compared with the conventional preparation methods.

In particular, when an aromatic methyl alcohol compound in which an electron donative group(s) such as an alkoxy group and methylenedioxy group, etc., is/are substituted on the aromatic ring is to be used, these has a tendency of higher reactivity. Thus, if the reaction is not carried out within the above-mentioned pH range, it can be considered that there is a higher possibility of generating by-product(s). That is, in the reaction of the present invention, it is particularly important to adjust the pH of the reaction solution.

In the reaction of the present invention, the compound to be used for pH adjustment of the reaction solution, etc. (hereinafter sometimes referred to as a pH adjusting agent.) is not particularly limited so long as it does not inhibit the reaction.

As the pH adjusting agent, there may be mentioned, for example, a hydroxide of an alkali metal and a hydroxide of an alkaline earth metal (for example, lithium hydroxide, sodium hydroxide, potassium hydroxide, rubidium hydroxide, cesium hydroxide, magnesium hydroxide, calcium hydroxide, strontium hydroxide, etc.), a carbonate of an alkali metal and a carbonate of an alkaline earth metal (for example, lithium carbonate, sodium carbonate, potassium carbonate, rubidium carbonate, cesium carbonate, magnesium carbonate, calcium carbonate, strontium carbonate), an alkoxide of an alkali metal and an alkoxide of an alkaline earth metal (for example, lithium methoxide, sodium methoxide, potassium methoxide, rubidium methoxide, cesium methoxide, calcium methoxide, magnesium methoxide), a carboxylate of an alkali metal and a carboxylate of an alkaline earth metal (for example, sodium acetate, potassium acetate, sodium oxalate, potassium oxalate), a phosphate of an alkali metal and a phosphate of an alkaline earth metal (for example, sodium phosphate, etc.), phosphoric acid, hydrochloric acid, sulfuric acid, boric acid, etc. As the pH adjusting agent, the above-mentioned buffer may be used.

The pH adjusting agent is preferably a hydroxide of an alkali metal, a hydroxide of an alkaline earth metal, a carbonate of an alkali metal, a carbonate of an alkaline earth metal, a phosphate of an alkali metal, a phosphate of an alkaline earth metal, phosphoric acid and boric acid. The above-mentioned pH adjusting agent may be used singly, or in admixture of two or more kinds. The above-mentioned compound may be used as such, or may be used by dissolving or suspending in water, an organic solvent such as an alcohol, etc., or a mixed solvent thereof.

A reaction temperature of the present invention is not particularly limited, and preferably carried out at 20° C. to 150° C., more preferably 40° C. to 140° C., particularly preferably 60° C. to 130° C. to avoid complexity in operation such as cooling, raising temperature, etc.

A reaction pressure of the reaction according to the present invention is not particularly limited. Also, the reaction conditions are not particularly limited, but in the reaction of the present invention, there are some cases where the above-mentioned safety becomes a problem due to generation of oxygen accompanied by the decomposition of hydrogen peroxide to be used, so that it is preferably carried out under an inert gas (for example, nitrogen, argon, helium) stream, or under an inert gas atmosphere.

In the reaction of the present invention, an order of addition of the starting materials is not particularly limited, and in the operation method of the present invention, by carrying out the operation method, for example, in which a peroxide is finally added to the reaction system dropwise continuously or stepwisely, etc., a condition of consumed peroxide can be confirmed during the reaction, whereby the reaction can be carried out while controlling the reaction conditions. By carrying out the operation method, the product can be prepared safety even when a peroxide with a higher concentration, for example, 60% aqueous hydrogen peroxide solution, etc., is used. Accordingly, in the preparation process of the present invention, it is preferred to employ a method in which a peroxide is finally added to the reaction media as an order of addition of the starting materials.

EXAMPLES

Next, the present invention is specifically explained by referring to Examples, but the scope of the present invention is not limited by these.

Example 1

Synthesis of Piperonal Using a Molybdenum Compound: Sodium Molybdate was Used, pH Value of the Reaction Solution; 4.0 to 5.0

In a glass-made reaction vessel equipped with a thermometer, a temperature controller, a dropping device and a stirring device were charged 213 g of toluene, 127.7 g (839 mmol) of piperonyl alcohol, 3.07 g (12.7 mmol) of sodium molybdate.dihydrate ($Na_2MoO_4 \cdot 2H_2O$), 4.32 g (12.7 mmol) of tetrabutyl ammonium hydrogen sulfate and 18.0 g of water. Then, to the mixture were added 0.50 g (3.20 mmol) of sodium dihydrogen phosphate.dihydrate and 2.05 g (5.72 mmol) of disodium hydrogen phosphate.1 dihydrate (a pH value at this time was 4.87.). An inner temperature of the reaction mixture was maintained from 84 to 85° C., and 52.0 g (0.92 mol) of 60% aqueous hydrogen peroxide was added dropwise to the mixture with 230 mmol/hr, while maintaining the pH of the reaction mixture to 4.0 to 5.0. After completion of the dropwise addition, the mixture was reacted for further one hour.

After completion of the reaction, the resulting reaction mixture was cooled to room temperature, and when the organic layer solution was quantitatively analyzed by HPLC (measured wavelength: 256 nm: absolute calibration method), then, the reaction yield of piperonal was 100.0% (Conversion of piperonyl alcohol: 99.0%).

Next, the solvent was distilled off from the organic layer solution, and the resulting white solid (piperonal) was analyzed, then, the physical properties thereof were as follows.

MS spectrum (CI-MS); 151 [M]$^+$
$^1$H-NMR spectrum (300 mHz, CDCl$_3$) δ (ppm); 6.07 (2H, s), 6.93 (1H, d, J=7.8 Hz), 7.32 (1H, d, J=1.5 Hz), 7.40, 7.42 (1H, dd, J=1.5 Hz), 9.81 (1H, s)

Example 2

Synthesis of Piperonal Using a Molybdenum Compound: Sodium Molybdate was Used, pH Value of the Reaction Solution; 0.01 to 1.0

In a glass-made reaction vessel equipped with a thermometer, a temperature controller, a dropping device and a stirring device were charged 213 g of toluene, 125.5 g (825 mmol) of piperonyl alcohol, 3.05 g (12.6 mmol) of sodium molybdate-.dihydrate (Na$_2$MoO$_4$.2H$_2$O), 4.18 g (12.3 mmol) of tetrabutyl ammonium hydrogen sulfate and 18.0 g of water. Then, to the mixture were added 0.30 g (1.92 mmol) sodium dihydrogen phosphate.dihydrate and 1.80 g (5.03 mmol) of disodium hydrogen phosphate.1 dihydrate, and a pH of the reaction mixture was adjusted to pH 0.5 by using phosphoric acid. An inner temperature of the reaction mixture was maintained from 84 to 85° C., and 70.0 g (1.24 mol) of 60% aqueous hydrogen peroxide was added dropwise to the mixture with 247 mmol/hr, while maintaining the pH of the reaction mixture to 0.01 to 0.08. After completion of the dropwise addition, the mixture was reacted for further one hour.

After completion of the reaction, when the organic layer solution of the resulting reaction mixture was quantitatively analyzed by HPLC (absolute calibration method), then, the reaction yield of piperonal was 80.0% (Conversion rate of piperonyl alcohol: 86.0%).

Example 3

Synthesis of Piperonal Using a Molybdenum Compound: Sodium Molybdate was Used, pH Value of the Reaction Solution; 1.0 to 2.0

In a glass-made reaction vessel equipped with a thermometer, a temperature controller, a dropping device and a stirring device were charged 215 g of toluene, 124.0 g (815 mmol) of piperonyl alcohol, 2.98 g (12.3 mmol) of sodium molybdate-.dihydrate (Na$_2$MoO$_4$.2H$_2$O), 4.18 g (12.3 mmol) of tetrabutyl ammonium hydrogen sulfate and 18.0 g of water. Then, to the mixture were added 0.50 g (3.21 mmol) of sodium dihydrogen phosphate.dihydrate and 1.77 g (4.94 mmol) of disodium hydrogen phosphate.1 dihydrate, and a pH of the reaction mixture was adjusted to pH 1.5 by using phosphoric acid. An inner temperature of the reaction mixture was maintained from 84 to 85° C., and 70.0 g (1.24 mol) of 60% aqueous hydrogen peroxide was added dropwise to the mixture with 247 mmol/hr while maintaining the pH of the reaction mixture to 1.0 to 2.0. After completion of the dropwise addition, the mixture was reacted for further one hour.

After completion of the reaction, when the organic layer solution of the resulting reaction mixture was quantitatively analyzed by HPLC (absolute calibration method), then, the reaction yield of piperonal was 95.0% (Conversion rate of piperonyl alcohol: 97.3%).

Example 4

Synthesis of Piperonal Using a Molybdenum Compound: Sodium Molybdate was Used, pH Value of the Reaction Solution; pH 2.0 to 4.0

In a glass-made reaction vessel equipped with a thermometer, a temperature controller, a dropping device and a stirring device were charged 213 g of toluene, 123.0 g (808 mmol) of piperonyl alcohol, 2.98 g (12.3 mmol) of sodium molybdate-.dihydrate (Na$_2$MoO$_4$.2H$_2$O), 4.18 g (12.3 mmol) of tetrabutyl ammonium hydrogen sulfate and 17.0 g of water. Then, to the mixture were added 0.50 g (3.21 mmol) of sodium dihydrogen phosphate.dihydrate and 1.77 g (4.94 mmol) of disodium hydrogen phosphate.1 dihydrate, and the pH of the reaction mixture was adjusted to pH 2.5 by using phosphoric acid. An inner temperature of the reaction mixture was maintained from 84 to 85° C., and 70.0 g (1.24 mol) of 60% aqueous hydrogen peroxide was added dropwise to the mixture with 247 mmol/hr, while maintaining the pH of the reaction mixture to 2.02 to 4.05. After completion of the dropwise addition, the mixture was reacted for further one hour.

After completion of the reaction, when the organic layer of the resulting reaction mixture was quantitatively analyzed by HPLC (absolute calibration method), then, the reaction yield of piperonal was 97.0% (Conversion rate of piperonyl alcohol: 99.6%).

Example 5

Synthesis of Piperonal Using a Molybdenum Compound: Sodium Molybdate was Used, pH Value of the Reaction Solution; 6.0 to 7.0

In a glass-made reaction vessel equipped with a thermometer, a temperature controller, a dropping device and a stirring device were charged 213 g of toluene, 127.5 g (838 mmol) of piperonyl alcohol, 3.07 g (12.7 mmol) of sodium molybdate-.dihydrate (Na$_2$MoO$_4$.2H$_2$O), 4.31 g (12.7 mmol) of tetrabutyl ammonium hydrogen sulfate and 18.0 g of water. Then, to the mixture were added 0.50 g (3.21 mmol) of sodium dihydrogen phosphate.dihydrate and 1.77 g (4.94 mmol) of disodium hydrogen phosphate.1 dihydrate, and the pH of the reaction mixture was adjusted to pH 6.3 by using 8N aqueous sodium hydroxide solution. An inner temperature of the reaction mixture was maintained from 84 to 85° C., and 56.8 g (1.00 mol) of 60% aqueous hydrogen peroxide was added dropwise to the mixture with 251 mmol/hr, while maintaining the pH of the reaction mixture to 6.0 to 7.0 by using 8N aqueous sodium hydroxide solution. After completion of the dropwise addition, the mixture was reacted for further one hour.

After completion of the reaction, when the organic layer solution of the resulting reaction mixture was quantitatively analyzed by HPLC (absolute calibration method), then, the reaction yield of piperonal was 99.0% (Conversion rate of piperonyl alcohol: 100.0%).

Example 6

Synthesis of Piperonal Using a Molybdenum Compound: Sodium Molybdate was Used, pH Value of the Reaction Solution; 8.0 to 9.0

In a glass-made reaction vessel equipped with a thermometer, a temperature controller, a dropping device and a stirring device were charged 213 g of toluene, 126.0 g (828 mmol) of piperonyl alcohol, 3.09 g (12.8 mmol) of sodium molybdate-.dihydrate ($Na_2MoO_4.2H_2O$), 4.18 g (12.3 mmol) of tetrabutyl ammonium hydrogen sulfate and 17.0 g of water. Then, to the mixture were added 0.50 g (3.21 mmol) of sodium dihydrogen phosphate.dihydrate and 1.77 g (4.94 mmol) of disodium hydrogen phosphate.1 dihydrate, and a pH of the reaction mixture was adjusted to pH 8.6 by using 8N aqueous sodium hydroxide solution. An inner temperature of the reaction mixture was maintained from 84 to 85° C., and 70.0 g (1.24 mol) of 60% aqueous hydrogen peroxide was added dropwise to the mixture with 247 mmol/hr while maintaining the pH of the reaction mixture to 8.0 to 9.0 by using 8N aqueous sodium hydroxide solution. After completion of the dropwise addition, the mixture was reacted for further one hour After completion of the reaction, when the organic layer solution of the resulting reaction mixture was quantitatively analyzed by HPLC (absolute calibration method), then, the reaction yield of piperonal was 94.0% (Conversion rate of piperonyl alcohol: 98.0%).

Comparative Example 1

Synthesis of Piperonal Using a Molybdenum Compound: Sodium Molybdate was Used, pH Value of the Reaction Solution; 10 to 11

In a glass-made reaction vessel equipped with a thermometer, a temperature controller, a dropping device and a stirring device were charged 224 g of toluene, 127.5 g (838 mmol) of piperonyl alcohol, 3.08 g (12.7 mmol) of sodium molybdate-.dihydrate ($Na_2MoO_4.2H_2O$), 4.30 g (12.7 mmol) of tetrabutyl ammonium hydrogen sulfate and 18.0 g of water. Then, to the mixture were added 0.80 g (5.13 mmol) of sodium dihydrogen phosphate.dihydrate and 2.05 g (5.72 mmol) of disodium hydrogen phosphate-1 dihydrate, and a pH of the reaction mixture was adjusted to pH 10.5 by using 8N aqueous sodium hydroxide solution. Next, an inner temperature of the reaction mixture was maintained from 94 to 95° C., and 71.0 g (1.25 mol) of 60% aqueous hydrogen peroxide was added dropwise to the mixture with 251 mmol/hr, while maintaining the pH of the reaction mixture to 10.07 to 10.96 by using 8N aqueous sodium hydroxide solution. After completion of the dropwise addition, the mixture was reacted for further one hour.

After completion of the reaction, when the organic layer solution of the resulting reaction mixture was quantitatively analyzed by HPLC (absolute calibration method), then, the reaction yield of piperonal was 67.8% (Conversion rate of piperonyl alcohol: 74.2%).

Example 7

Synthesis of Piperonal Using a Molybdenum Compound: Sodium Molybdate was Used, pH Value of the Reaction Solution; 6.0 to 7.0

In a glass-made reaction vessel equipped with a thermometer, a temperature controller, a dropping device and a stirring device were charged 38 g of toluene, 20.0 g (131 mmol) of piperonyl alcohol, 0.65 g (2.69 mmol) of sodium molybdate-.dihydrate ($Na_2MoO_4.2H_2O$), 0.91 g (2.68 mmol) of tetrabutyl ammonium hydrogen sulfate and 2.5 g of water. Then, to the mixture were added 0.11 g (0.71 mmol) of sodium dihydrogen phosphate.dihydrate and 0.33 g (0.92 mmol) of disodium hydrogen phosphate.1 dihydrate, and a pH of the reaction mixture was adjusted to pH 6.0. An inner temperature of the reaction mixture was maintained from 75 to 79° C., 7.7 ml (158 mmol) of 60% aqueous hydrogen peroxide was added dropwise to the mixture, while maintaining the pH of the reaction mixture to pH 6.0 to 7.0 by using 8 mol/L aqueous sodium hydroxide solution. The reaction was stopped when 91% of the starting material, piperonyl alcohol was consumed.

After completion of the reaction, when the organic layer of the resulting reaction mixture was quantitatively analyzed by HPLC (absolute calibration method), then, the reaction yield of piperonal was 88.0%.

Example 8

Synthesis of Piperonal Using a Molybdenum Compound: Molybdenum Hexacarbonyl was Used, pH Value of the Reaction Solution; 6.0 to 7.0

In the same manner as in Example 7 using the same amounts of reagents, the reaction was carried out except for changing sodium molybdate.dihydrate to molybdenum hexacarbonyl ($Mo(CO)_6$), and the reaction was stopped when 87% of the starting material, piperonyl alcohol was consumed. After completion of the reaction, when the organic layer solution of the resulting reaction mixture was quantitatively analyzed by HPLC (absolute calibration method), then, the reaction yield of piperonal was 84.0%.

Example 9

Synthesis of Piperonal Using a Molybdenum Compound: Molybdenum Trioxide was Used, pH Value of the Reaction Solution; 6.0 to 7.0

In the same manner as in Example 7 using the same amounts of reagents, the reaction was carried out except for changing sodium molybdate.dihydrate to molybdenum trioxide ($MoO_3$), and the reaction was stopped when 72% of the starting material, piperonyl alcohol was consumed. After completion of the reaction, when the organic layer solution of the resulting reaction mixture was quantitatively analyzed by HPLC (absolute calibration method), then, the reaction yield of piperonal was 72.0%.

Example 10

Synthesis of Piperonal Using a Molybdenum Compound: Molybdenum Dioxide was Used, pH Value of the Reaction Solution; 6.0 to 7.0

In the same manner as in Example 7 using the same amounts of reagents, the reaction was carried out except for changing sodium molybdate.dihydrate to molybdenum dioxide ($MoO_2$), and the reaction was stopped when 92% of the starting material, piperonyl alcohol was consumed. After completion of the reaction, when the organic layer solution of the resulting reaction mixture was quantitatively analyzed by HPLC (absolute calibration method), then, the reaction yield of piperonal was 89.0%.

Example 11

Synthesis of Piperonal Using a Molybdenum Compound: Sodium Molybdate was Used, without Solvent, pH Value of the Reaction Solution; 6.0 to 7.0

In a glass-made reaction vessel equipped with a thermometer, a temperature controller, a dropping device and a stirring device were charged 126.0 g (828 mmol) of piperonyl alcohol, 1.03 g (4.26 mmol) of sodium molybdate.dihydrate ($Na_2MoO_4 \cdot 2H_2O$), 1.46 g (4.30 mmol) of tetrabutyl ammonium hydrogen sulfate and 18.0 g of water. Then, to the mixture were added 0.60 g (3.85 mmol) of sodium dihydrogen phosphate.dihydrate and 2.05 g (5.72 mmol) of disodium hydrogen phosphate.1 dihydrate, and a pH of the reaction mixture was adjusted to pH 6.5 by using 8 mol/L aqueous sodium hydroxide solution. Next, an inner temperature of the reaction mixture was maintained from 84 to 85° C., and 61.0 g (1.08 mol) of 60% aqueous hydrogen peroxide was added dropwise to the mixture with 269 mmol/hr, while maintaining the pH of the reaction mixture to 6.0 to 7.0 by using 8N aqueous sodium hydroxide solution. After completion of the dropwise addition, the mixture was reacted for further one hour.

After completion of the reaction, when the organic layer solution of the resulting reaction mixture was quantitatively analyzed by HPLC (absolute calibration method), then, the reaction yield of piperonal was 96.0% (Conversion rate of piperonyl alcohol: 99.4%).

Example 12

Synthesis of Piperonal Using a Molybdenum Compound: Sodium Molybdate was Used, No Buffer (a Phosphoric Acid Compound), pH Value of the Reaction Solution; 6.0 to 7.0

In a glass-made reaction vessel equipped with a thermometer, a temperature controller, a dropping device and a stirring device were charged 125.0 g (822 mmol) of piperonyl alcohol, 2.98 g (12.3 mmol) of sodium molybdate.dihydrate ($Na_2MoO_4 \cdot 2H_2O$), 4.19 g (12.3 mmol) of tetrabutyl ammonium hydrogen sulfate and 18.0 g of water, and a pH of the reaction mixture was adjusted to pH 6.5 by using 8 mol/L aqueous sodium hydroxide solution. Next, an inner temperature of the reaction mixture was maintained from 84 to 85° C., 70.0 g (1.25 mol) of 60% aqueous hydrogen peroxide was added dropwise to the mixture with 247 mmol/hr, while maintaining the pH of the reaction mixture to 6.0 to 7.0 by using 8N aqueous sodium hydroxide solution. After completion of the dropwise addition, the mixture was reacted for further one hour.

After completion of the reaction, the organic layer solution of the resulting reaction mixture was quantitatively analyzed by HPLC (absolute calibration method), then, the reaction yield of piperonal was 95.0% (Conversion rate of piperonyl alcohol: 99.9%).

Comparative Example 2

Synthesis of Piperonal Using a Molybdenum Compound: Sodium Molybdate was Used, No at Least One Salt Selected from a Quaternary Ammonium Salt and an Organic Phosphonium Salt, pH Value of the Reaction Solution; 6.0 to 7.0

In the same manner as in Example 5 using the same amounts of reagents, the reaction was carried out except for not using at least one salt selected from a quaternary ammonium salt and an organic phosphonium salt. After completion of the reaction, when the organic layer solution of the resulting reaction mixture was quantitatively analyzed by HPLC (absolute calibration method), then, no piperonal was obtained (Conversion rate of piperonyl alcohol: 6.0%).

Comparative Example 3

Synthesis of Piperonal Using a Molybdenum Compound; See Operation Method of Patent Literature 1: JP 1111-158107A In a glass-made reaction vessel equipped with a thermometer, a temperature controller, a dropping device and a stirring device were charged 1.21 g (5.00 mmol) of sodium molybdate.dihydrate ($Na_2MoO_4 \cdot 2H_2O$), 1.70 g (5.00 mmol) of tetrabutyl ammonium hydrogen sulfate and 90.0 g (794 mmol) of 30% aqueous hydrogen peroxide, and the mixture was vigorously stirred at room temperature for 10 minutes. Then, to the mixture was added dropwise 220 mL of a toluene solution containing 76.0 g (500 mmol) of piperonyl alcohol (a pH of the reaction mixture at this time was 0.1). After completion of the dropwise addition, the reaction mixture was stirred at 70° C. for 5 hours. After completion of the reaction, when the organic layer solution of the resulting reaction mixture was quantitatively analyzed by HPLC (absolute calibration method), then, the yield of the objective material, piperonal was only 15.2% (Conversion rate of piperonyl alcohol: 43.5%).

Example 13

Synthesis of Piperonal Using a Tungsten Compound: Sodium Tungstate was Used, pH Value of the Reaction Solution; 5.5 to 6.5

In a glass-made reaction vessel equipped with a thermometer, a temperature controller, a dropping device and a stirring device were charged 220 ml of xylene, 76.01 g (500 mmol) of piperonyl alcohol, 1.65 g (5.0 mmol) of sodium tungstate.dihydrate ($Na_2WO_4 \cdot 2H_2O$), 1.70 g (5.0 mmol) of tetrabutyl ammonium hydrogen sulfate and 9.42 g of water. Then, to the mixture were added 2.34 g (1.6 mmol) of sodium dihydrogen phosphate.dihydrate and 3.56 g (1.0 mmol) of disodium hydrogen phosphate.1 dihydrate, and a pH of the reaction mixture was adjusted to pH 6.0. Next, an inner temperature of the reaction mixture was maintained from 94 to 95° C., 48.0 ml (991 mmol) of 60% aqueous hydrogen peroxide was added dropwise to the mixture with 141 mmol/hr, while maintaining the pH of the reaction mixture to 5.5 to 6.5 by using 8 mol/L aqueous sodium hydroxide solution. After completion of the reaction, the resulting reaction mixture was cooled to room temperature, and the organic layer was separated as a solution. The resulting organic layer solution was washed with 80 mL of 1 mol/L aqueous sodium hydroxide solution, and the solvent, xylene was distilled off with (1.3 kPa/132° C.) to obtain 67.7 g of piperonal as white solid (yield: 89.3%, based on piperonyl alcohol).

The physical properties of the resulting compound (piperonal) were as follows.

HPLC purity 94.9% (measured wavelength: 256 nm)
MS spectrum (CI-MS); 151 $[M]^+$.
$^1$H-NMR spectrum (300 mHz, $CDCl_3$) δ (ppm); 6.07 (2H, s), 6.93 (1H, d, J=7.8 Hz), 7.32 (1H, d, J=1.5 Hz), 7.40, 7.42 (1H, dd, J=1.5 Hz), 9.81 (1H, s).

Example 14

Synthesis of Piperonal Using a Tungsten Compound: Sodium Tungstate was used, pH Value of the Reaction Solution; 6.0 to 7.0

In the same manner as in Example 13 using the same amounts of reagents, the reaction was carried out except for changing sodium tungstate.dihydrate to tungstic acid (hydrogen tetraoxotungstic(VI) acid; $H_2WO_4$), and the reaction was stopped when 70% of the starting material, piperonyl alcohol was consumed. After completion of the reaction, when the organic layer solution of the resulting reaction mixture was quantitatively analyzed by HPLC (absolute calibration method), the yield of piperonal was 69.0%.

Example 15

Synthesis of Piperonal Using a Tungsten Compound: Sodium Tungstate was Used, pH Value of the Reaction Solution; 6.0 to 7.0

In the same manner as in Example 13 using the same amounts of reagents, the reaction was carried out except for changing sodium tungstate.dihydrate to tungsten trioxide ($WO_3$), and the reaction was stopped when 74% of the starting material, piperonyl alcohol was consumed. After completion of the reaction, when the organic layer solution of the resulting reaction mixture was quantitatively analyzed by HPLC (absolute calibration method), the yield of piperonal was 71.0%.

Example 16

Synthesis of Piperonal Using a Tungsten Compound: Using Sodium Tungstate, pH Value of the Reaction Solution; 7.0

In the same manner as in Example 13 using the same amounts of reagents, the reaction was carried out except for changing the pH value of the reaction mixture to 7.0 by using 8 mol/L aqueous sodium hydroxide solution. After completion of the reaction, when the organic layer solution of the resulting reaction mixture was quantitatively analyzed by HPLC (absolute calibration method), the yield of piperonal was 95.4%.

Example 17

Synthesis of Piperonal Using a Tungsten Compound: pH Value of the Reaction Solution; 3.0

In the same manner as in Example 13 using the same amounts of reagents, the reaction was carried out except for changing the pH value of the reaction mixture to 3.0 by using phosphoric acid and sodium dihydrogen phosphate. After completion of the reaction, when the organic layer solution of the resulting reaction mixture was quantitatively analyzed by HPLC (absolute calibration method), the yield of piperonal was 54.5%.

Comparative Example 4

Synthesis of Piperonal Using a Tungsten Compound; Using Sodium Tungstate, pH Value of the Reaction Solution: 9.0

In the same manner as in Example 13 using the same amounts of reagents, the reaction was carried out except for changing the pH value of the reaction mixture to 9.0 by using 8 mol/L aqueous sodium hydroxide solution. After completion of the reaction, when the organic layer solution of the resulting reaction mixture was quantitatively analyzed by HPLC (absolute calibration method), the yield of piperonal was only 21.7%.

Comparative Example 5

Synthesis of Piperonal Using a Tungsten Compound; Using Sodium Tungstate, pH Value of the Reaction Solution: 1.0

In the same manner as in Example 13 using the same amounts of reagents, the reaction was carried out except for changing the pH value of the reaction mixture to 1.0 by using phosphoric acid. When the organic layer solution of the resulting reaction mixture was quantitatively analyzed by HPLC (absolute calibration method), then, the yield of piperonal was only 38.4%.

Example 18

Synthesis of Piperonal Using a Tungsten Compound; Using Sodium Tungstate, Using Tetrabutyl Ammonium Chloride as a Quaternary Ammonium Salt In a glass-made reaction vessel equipped with a thermometer, a temperature controller, a dropping device and a stirring device were charged 220 ml of xylene, 76.00 g (500 mmol) of piperonyl alcohol, 1.65 g (5.0 mmol) of sodium tungstate.dihydrate ($Na_2WO_4.2H_2O$), 1.39 g (5.0 mmol) of tetrabutyl ammonium chloride and 9.42 g of water. Then, to the mixture were added 2.34 g (1.6 mmol) of sodium dihydrogen phosphate.dihydrate and 3.56 g (1.0 mmol) of disodium hydrogen phosphate.1 dihydrate, and a pH of the reaction mixture was adjusted to pH 6.0. Next, an inner temperature of the reaction mixture was maintained from 94 to 95° C., 48.0 ml (991 mmol) of 60% aqueous hydrogen peroxide was added dropwise with 141 mmol/hr, while maintaining the pH of the reaction mixture to 5.5 to 6.5 by using 8 mol/L aqueous sodium hydroxide solution. After completion of the reaction, the resulting reaction mixture was cooled to room temperature, and the organic layer was separated as a solution. When the organic layer of the resulting reaction mixture was quantitatively analyzed by HPLC (absolute calibration method), then the yield of piperonal was 69.8 g, and the reaction yield was 93.0%.

Example 19

Synthesis of Piperonal Using a Tungsten Compound; Using Sodium Tungstate, and Using Tetraphenylphosphonium Chloride as an Organic Phosphonium Salt In a glass-made reaction vessel equipped with a thermometer, a temperature controller, a dropping device and a stirring device were charged 220 ml of xylene, 76.00 g (500 mmol) of piperonyl alcohol, 1.65 g (5.0 mmol) of sodium tungstate.dihydrate ($Na_2WO_4.2H_2O$), 1.87 g (5.0 mmol) of tetraphenylphosphonium chloride and 9.42 g of water. Then, to the mixture were added 2.34 g (1.6 mmol) of sodium dihydrogen phosphate.dihydrate and 3.56 g (1.0 mmol) of disodium hydrogen phosphate.1 dihydrate, and a pH value of the reaction mixture was adjusted to pH 6.0. Next, an inner temperature of the reaction mixture was maintained from 94 to 95° C., and 48.0 ml (991 mmol) of 60% aqueous hydrogen peroxide was added dropwise to the mixture with 141 mmol/hr, while maintaining the pH of the reaction mixture to 5.5 to 6.5 by using 8 mol/L aqueous sodium hydroxide solution. After completion of the reaction, the resulting reaction mixture was cooled to room temperature, and the organic layer was separated as a solution. When the organic layer solution of the resulting reaction mixture was quantitatively analyzed by HPLC (absolute calibration method), the yield of piperonal was 68.5 g, and a reaction yield was 91.3%.

Example 20

Synthesis of Piperonal Using a Tungsten Compound; Sodium Tungstate was Used, No Buffer (a Phosphoric Acid Compound)

In a glass-made reaction vessel equipped with a thermometer, a temperature controller, a dropping device and a stirring device were charged 220 ml of xylene, 76.00 g (500 mmol) of piperonyl alcohol, 1.65 g (5.0 mmol) of sodium tungstate.dihydrate ($Na_2WO_4.2H_2O$), 1.70 g (5.0 mmol) of tetrabutyl ammonium hydrogen sulfate and 9.42 g of water. Next, an inner temperature of the reaction mixture was maintained from 94 to 95° C., and 48.0 ml (991 mmol) of 60% aqueous hydrogen peroxide was added dropwise to the mixture with 141 mmol/hr, while maintaining the pH value of the reaction mixture to 5.5 to 6.5 by using 8 mol/L aqueous sodium hydroxide solution. After completion of the reaction, the resulting reaction mixture was cooled to room temperature, and the organic layer was separated as a solution. When the organic layer of the resulting reaction mixture was quantitatively analyzed by HPLC (absolute calibration method), the yield of piperonal was 67.18 g, and a reaction yield was 89.5%.

Example 21

Synthesis of Anisole Using a Tungsten Compound: Using Sodium Tungstate

In a glass-made reaction vessel equipped with a thermometer, a temperature controller, a dropping device and a stirring device were charged 79 ml of xylene, 138.16 g (1 mol) of 4-methoxybenzyl alcohol, 3.30 g (0.01 mol) of sodium tungstate.dihydrate ($Na_2WO_4.2H_2O$) and 3.40 g (0.01 mol) of tetrabutyl ammonium hydrogen sulfate. Then, to the mixture were added 4.68 g (0.03 mol) of sodium dihydrogen phosphate and 7.16 g (0.02 mol) of disodium hydrogen phosphate, and a pH value of the reaction mixture was adjusted to pH 6.0. Next, an inner temperature of the reaction mixture was maintained from 94 to 95° C., and 94.33 g (1.56 mol) of 60% aqueous hydrogen peroxide was added dropwise to the mixture with 18 g (0.3 mol)/hr, while maintaining the pH of the reaction mixture to 5.5 to 6.5 by using 8 mol/L aqueous sodium hydroxide solution. After completion of the reaction, the resulting reaction mixture was cooled to room temperature, and the organic layer was separated as a solution. The resulting organic layer solution was washed with 1 mol/L sodium hydroxide solution, and the solvent, xylene was distilled off under reduced pressure. The resulting concentrate (crude anisaldehyde) was purified by distillation (109° C./1.3 kPa) to obtain 118.28 g of anisaldehyde as colorless liquid (obtained yield: 86.9%, based on anisalcohol).

Example 22

Synthesis of Benzaldehyde Using a Tungsten Compound: Sodium Tungstate was Used

In a glass-made vessel equipped with a thermometer, a temperature controller, a dropping device and a stirring device were charged 79 ml of xylene, 108.14 g (1.00 mol) of benzylalcohol, 3.30 g (0.01 mol) of sodium tungstate.dihydrate ($Na_2WO_4.2H_2O$) and 3.40 g (0.01 mol) of tetrabutyl ammonium hydrogen sulfate. Then, 4.68 g (0.03 mol) of sodium dihydrogen phosphate and 7.16 g (0.02 mol) of disodium hydrogen phosphate were mixed and a pH of the reaction mixture was adjusted to 6.0. Next, an inner temperature of the reaction mixture was maintained from 94 to 95° C., and 80.38 g (1.34 mol) of 60% aqueous hydrogen peroxide was added dropwise to the mixture with 18.00 g (0.3 mol)/hr, while maintaining the pH of the reaction mixture to 5.5 to 6.5 by using 8 mol/L aqueous sodium hydroxide solution. After completion of the reaction, the resulting reaction mixture was cooled to room temperature, and the organic layer was separated as a solution. The resulting organic layer solution was washed with 1 mol/L sodium hydroxide solution, and the solvent, xylene was distilled off under reduced pressure. The resulting concentrate (crude benzaldehyde) was purified by distillation (66° C./2.5 kPa) to obtain 100.51 g of benzaldehyde as colorless liquid (obtained yield: 94.7%, based on benzylalcohol).

Comparative Example 6

Synthesis of Piperonal Using a Tungsten Compound; See Operation Method of Patent Literature 1: JP H11-158107A In a glass-made vessel equipped with a thermometer, a temperature controller, a dropping device and a stirring device were charged 1.65 g (5.00 mmol) of sodium tungstate.dihydrate ($Na_2WO_4.2H_2O$), 1.70 g (5.00 mmol) of tetrabutyl ammonium hydrogen sulfate and 90.00 g (750 mmol) of 30% aqueous hydrogen peroxide, and the mixture was vigorously stirred at room temperature for 10 minutes. Then, 220 ml of a toluene solution containing 76.01 g (500 mmol) of piperonyl alcohol was added thereto dropwise. The pH value of the reaction mixture was a pH of 1.6. After dropping addition, the reaction mixture was stirred at 70° C. for 5 hours. After completion of the reaction, the organic layer solution of the resulting reaction mixture was quantitatively analyzed by HPLC (absolute calibration method), then, the reaction yield of piperonal was as little as 24.9% (Conversion rate of piperonyl alcohol: 55.6%).

Comparative Example 7

Synthesis of Piperonal Using a Vanadium Compound: Vanadium Pentoxide was Used, pH Value of the Reaction Solution; 6.0-7.0

In the same manner as in Example 12 using the same amounts of reagents, the reaction was carried out except for changing sodium tungstate.dihydrate to vanadium pentoxide ($V_2O_5$) for the same hours, but the starting material, piperonyl alcohol was consumed only 13%. After completion of the reaction, when the resulting reaction mixture was quantitatively analyzed (absolute calibration method), then, the yield of piperonal was only 2%.

Comparative Examples 8 to 18

Synthesis of Piperonal Using the Other Metallic Catalysts

In the same manner as in Example 7 using the same amounts of reagents except for changing sodium tungstate.dihydrate to various metals shown in the following Table 1, and the reaction was carried out for 5 hours. The results are shown in Table 1.

Comparative Example 19

Synthesis of Piperonal (No Metallic Compound): pH Value of the Reaction Solution; 6.0-7.0

In the same manner as in Example 7 using the same amounts of reagents except for using the metallic compound such as sodium molybdate.dihydrate or sodium tungstate.dihydrate, etc., and the reaction was carried out for 4 hours. As a result, as shown in Table 1, whereas the starting material, piperonyl alcohol was consumed 4% thereof, and when the resulting reaction mixture was quantitatively analyzed (absolute calibration method), no piperonal was found to be formed.

TABLE 1

| Comparative example | Metallic compound | POH Conversion (%) | PAL Selectivity (%) | PAL Yield (%) |
|---|---|---|---|---|
| 7 | $V_2O_5$ | 13 | 15 | 2 |
| 8 | $KMnO_4$ | 8 | — | Trace |
| 9 | $K_2MnO_4$ | 5 | — | Trace |
| 10 | $Mn(acac)_3$ | 2 | — | Trace |
| 11 | $MnCl_2 \cdot 4H_2O$ | 6 | — | Trace |
| 12 | $Fe_2O_3$ | 6 | — | Trace |
| 13 | $FeCl_3$ | 10 | — | Trace |
| 14 | $LiCoO_2$ | 7 | — | Trace |
| 15 | $CoCl_2 \cdot 6H_2O$ | 7 | — | Trace |
| 16 | $CuCl_2$ | 17 | — | Trace |
| 17 | $ReO_3$ | 4 | — | Trace |
| 18 | $Na_2CrO_4$ | 18 | 53 | 10 |
| 19 | None | 4 | — | — |

*1 POH: piperonyl alcohol
*2 PAL: piperonal
*3 Conversion, selectivity and yield were calculated from HPLC analysis (absolute calibration method).

UTILIZABILITY IN INDUSTRY

The present invention relates to a process for preparing an aromatic aldehyde compound which comprises reacting an aromatic methyl alcohol compound and a peroxide under a pH value of a reaction solution being a pH of 0.01 or higher and less than 10 in the presence of at least one or more metallic compound selected from a molybdenum compound and a tungsten compound, and a quaternary ammonium salt.

The aromatic aldehyde compound obtained by the process of the present invention is a compound useful, for example, as various chemical products such as medical and agricultural chemicals and organic materials, and their starting materials and intermediates.

The invention claimed is:

1. A process for preparing an aromatic aldehyde compound represented by the formula (2);

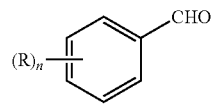

(2)

wherein R represents a halogen atom, a hydrocarbon group having 1 to 12 carbon atoms, an alkyloxy group having 1 to 12 carbon atoms, a phenyloxy group, a naphthyloxy group, a benzyloxy group or a phenethyloxy group, each group of which may have a substituent(s); n is an integer of 0 to 5; and when n is 2 or more, Rs may form a ring by combining with each other, which comprises reacting an aromatic methyl alcohol compound represented by the formula (1);

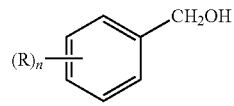

(1)

wherein R and n have the same meanings as defined above, and a peroxide under a pH value of a reaction solution being pH 0.5 or higher and less than 9, in the presence of at least one metallic compound of a molybdenum compound, and at least one salt selected from a quaternary ammonium salt and an organic phosphonium salt, wherein the aromatic aldehyde compound of the formula (2) is at least one selected from the group consisting of the following formulae (4) to (7):

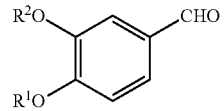

(4)

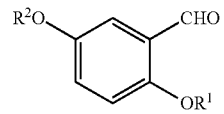

(5)

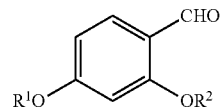

(6)

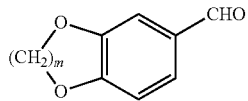

(7)

wherein $R^1$ and $R^2$ each represents a hydrogen atom, a hydrocarbon group having 1 to 12 carbon atoms, an alkyl group having 1 to 12 carbon atoms, a phenyl group, a naphthyl group, a benzyl group or a phenethyl group, each group of which may have a substituent(s), and m is 1 or 2.

2. A process for preparing an aromatic aldehyde compound represented by the formula (2);

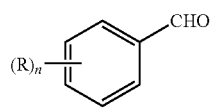

(2)

wherein R represents a halogen atom, a hydrocarbon group having 1 to 12 carbon atoms, an alkyloxy group having 1 to 12 carbon atoms, a phenyloxy group, a naphthyloxy group, a benzyloxy group or a phenethyloxy group, each group of which may have a substituent(s); n is an integer of 0 to 5; and when n is 2 or more, Rs may form a ring by combining with each other, which comprises reacting an aromatic methyl alcohol compound represented by the formula (1);

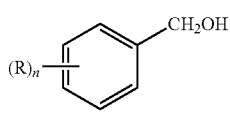

(1)

wherein R and n have the same meanings as defined above, and a peroxide while maintaining a pH value of a reaction solution to a pH of 3 or higher and less than 8 in the presence of at least one metallic compound of a tungsten compound, and at least one salt selected from a quaternary ammonium salt and an organic phosphonium salt, wherein the aromatic aldehyde compound of the formula (2) is at least one selected from the group consisting of the following formulae (4) to (7):

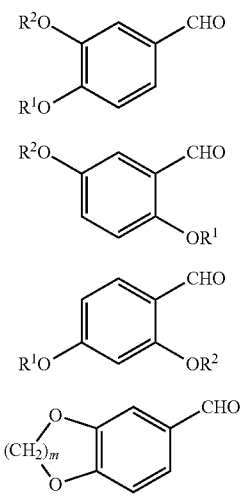

wherein $R^1$ and $R^2$ each represents a hydrogen atom, a hydrocarbon group having 1 to 12 carbon atoms, an alkyl group having 1 to 12 carbon atoms, a phenyl group, a naphthyl group, a benzyl group or a phenethyl group, each group of which may have a substituent(s), and m is 1 or 2, wherein the quaternary ammonium salt is at least one selected from the group consisting of tetrabutyl ammonium hydrogen sulfate, tetra-n-hexyl ammonium hydrogen sulfate, tetrabutyl ammonium chloride and tetrabutyl ammonium bromide, and wherein the organic phosphonium salt is at least one selected from the group consisting of tetrabutylphosphonium chloride, tetrabutylphosphonium bromide, tetraphenylphosphonium chloride and tetraphenylphosphonium bromide.

3. The preparation process according to claim 1, wherein the reaction is carried out by further adding at least one buffer selected from a phosphoric acid compound, a boric acid compound and a carbonic acid compound.

4. The preparation process according to claim 1, wherein the metallic compound is a molybdenum compound, and the pH value of the reaction solution is a pH of 0.8 or higher and a pH of less than 9.

5. The preparation process according to claim 2, wherein the metallic compound is a tungsten compound, and the pH value of the reaction solution is a pH of 4 to 7.5.

6. The preparation process according to claim 1, wherein the peroxide is hydrogen peroxide.

7. The preparation process according to claim 1, wherein the aromatic aldehyde compound is a compound represented by the formula (7) where m is 1.

8. The preparation process according to claim 6, wherein an amount of the hydrogen peroxide to be used is 0.1 to 5 mol based on 1 mol of the aromatic methyl alcohol compound.

9. The preparation process according to claim 1, wherein an amount of at least one of the metallic compound of the molybdenum compound is 0.0001 to 0.10 mol based on 1 mol of the aromatic methyl alcohol compound.

10. The preparation process according to claim 1, wherein the molybdenum compound is at least one compound selected from an alkali molybdate compound, molybdenum dioxide, molybdenum trioxide, phosphomolybdic acid, an alkali phosphomolybdate compound, and molybdenum hexacarbonyl.

11. The preparation process according to claim 2, wherein the tungsten compound is at least one compound selected from an alkali tungstate compound, tungsten trioxide, phosphotungstic acid, an alkali phosphotungstate compound, and tungsten hexacarbonyl.

12. The preparation process according to claim 3, wherein the phosphoric acid compound is at least one compound selected from phosphoric acid (orthophosphoric acid, pyrophosphoric acid, metaphosphoric acid), sodium phosphate, potassium phosphate, sodium monohydrogen phosphate, sodium dihydrogen phosphate, potassium monohydrogen phosphate, potassium dihydrogen phosphate, and ammonium phosphate.

13. The preparation process according to claim 1, wherein the pH is adjusted by at least one compound selected from a hydroxide of an alkali metal, a hydroxide of an alkaline earth metal, a carbonate of an alkali metal, a carbonate of an alkaline earth metal, a phosphate of an alkali metal and a phosphate of an alkaline earth metal, phosphoric acid, hydrochloric acid and sulfuric acid.

14. The preparation process according to claim 1, wherein the reaction is carried out without solvent.

15. The preparation process according to claim 1, wherein the pH value of the reaction solution is a pH of 1 or higher and a pH of less than 9.

16. The preparation process according to claim 1, wherein the aromatic aldehyde compound is piperonal and the molybdenum compound is sodium molbdate.

17. The preparation process according to claim 1, wherein the aromatic aldehyde compound is piperonal and the molybdenum compound is molybdenum hexacarbonyl, molybdenum trioxide or molybdenum dioxide.

18. The preparation process according to claim 2, wherein the aromatic aldehyde compound is piperonal and the tungsten compound is sodium tungstate.

* * * * *